United States Patent
Snyder et al.

[11] Patent Number: 6,120,449
[45] Date of Patent: Sep. 19, 2000

[54] METHOD AND APPARATUS FOR COMPENSATING FOR INOPERATIVE ELEMENTS IN ULTRASONIC TRANSDUCER ARRAY

[75] Inventors: Jonathan E. Snyder, Whitefish Bay, Wis.; Mir Said Seyed-Bolorforosh, Palto Alto, Calif.

[73] Assignee: General Electric Company, Milwaukee, Wis.

[21] Appl. No.: 09/200,077

[22] Filed: Nov. 25, 1998

[51] Int. Cl.[7] ...................................................... A61B 8/00
[52] U.S. Cl. ............................................................ 600/447
[58] Field of Search .................................... 600/437, 443, 600/447, 454–456, 459; 73/625–626; 367/7, 11, 138

[56] References Cited

U.S. PATENT DOCUMENTS

| | | | |
|---|---|---|---|
| 3,873,947 | 3/1975 | Johnson | 333/72 |
| 4,698,807 | 10/1987 | Marwood et al. | 371/11 |
| 4,893,284 | 1/1990 | Magrane | 367/12 |
| 5,520,187 | 5/1996 | Snyder | 128/661.01 |
| 5,676,149 | 10/1997 | Yao | 128/660.01 |
| 5,902,241 | 5/1999 | Seyed-Bolorforosh et al. | 600/443 |

*Primary Examiner*—Francis J. Jaworski
*Attorney, Agent, or Firm*—Dennis M. Flaherty; Christian G. Cabou; Phyllis Y. Price

[57] ABSTRACT

A method and an apparatus for compensating for fully or partially inoperative elements in an ultrasonic transducer array. The inoperative elements are compensated for by "bridging" or "shorting" them to fully operative elements. This compensation technique can be applied to one-dimensional or multi-dimensional transducer arrays. A bridge between a fully or partially inoperative element and an adjacent fully operative element can be achieved by physically shorting the elements somewhere in the signal chain or by electrically connecting the elements via switches, e.g., of a multiplexer. The state of the multiplexer switches (i.e., open or closed) is controlled by loading MUX State control data into a flash memory located on-board the probe. This MUX State control data includes switch settings for connecting a defective element to an adjacent fully functional element in the transducer array.

20 Claims, 6 Drawing Sheets

FIG. 13 ns in ULTRASONIC TRANSDUCER ARRAY

FIELD OF THE INVENTION

This invention generally relates to ultrasound imaging, primarily clinical ultrasound images as well as industrial ultrasonic images. In particular, the invention relates to methods of compensating for inoperative elements in an ultrasonic transducer array.

BACKGROUND OF THE INVENTION

Conventional ultrasound imaging systems comprise an array of ultrasonic transducer elements which are used to transmit an ultrasound beam and then receive the reflected beam from the object being studied. For ultrasound imaging, a one-dimensional array typically has a multiplicity of transducer elements arranged in a line and driven with separate voltages. By selecting the time delay (or phase) and amplitude of the applied voltages, the individual transducer elements can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the object.

The same principles apply when the transducer array is employed to receive the reflected sound (receiver mode). The voltages produced at the receiving transducers are delayed and summed so that the net signal is indicative of the ultrasound reflected from a single focal point in the object. As with the transmission mode, this focused reception of the ultrasonic energy is achieved by imparting a separate time delay (and/or phase shift) and gain to the signal from each receiving transducer.

A phased-array ultrasound transducer consists of an array of small piezoelectric elements, with an independent electrical connection to each element. In most conventional transducers the elements are arranged in a single row, spaced at a fine pitch (one-half to one acoustic wavelength on center). As used herein, the term "1D" array refers to a single-row transducer array having an elevation aperture which is fixed and a focus which is at a fixed range; the term "1.5D" array refers to a multi-row array having an elevation aperture, shading, and focusing which are dynamically variable, but symmetric about the centerline of the array; and the term "2D" array refers to a multi-row transducer array having an elevation geometry and performance which are comparable to azimuth, with full electronic apodization, focusing and steering. Electronic circuitry connected to the elements uses time delays and perhaps phase rotations to control the transmitted and received signals and form ultrasound beams which are steered and focused throughout the imaging plane. For some ultrasound systems and probes, the number of transducer elements in the probe exceeds the number of channels of beamformer electronics in the system. In these cases an electronic multiplexer is used to dynamically connect the available channels to different (typically contiguous) subsets of the transducer elements during different portions of the image formation process.

With the advent of multidimensional probes and the high element counts required to create this type of diagnostic imaging device, the problems associated with the manufacture of ultrasonic transducer arrays are mounting. The problem of "dead" (i.e., fully inoperative) or "weak" (i.e., partially inoperative) elements is of particular concern as the industry moves toward the manufacture of two-dimensional arrays having element counts exceeding 1,000. Process or material errors are often responsible for the creation of a probe without all elements fully functional. Because the specifications regarding element functionality are quite tight, there is little tolerance for dead or weak elements in current probe manufacturing. These requirements focus particular attention on the performance of the manufacturing processes and directly control the amount of manufacturing scrap. Dead element specifications are tight because the effect of this defect on the image quality can be significant, particularly in the near field of the image where a fewer number of elements are used to form the beam. In this case a dead or weak element becomes a significant part of the aperture used to create the image, resulting in an intensity loss at the acoustic line in question.

Currently, probe technology is delivering element counts on the order of 200 or less with processes providing reasonable manufacturing yields. However, new technology is demanding probes with element counts greater the 1,000. Utilizing current production processes, the dead or weak element probability delivers unacceptable yield at this element density. Other than developing new or tighter tolerance manufacturing processes, there are two solutions to this problem. The first is to develop a compensation scheme within the system to detect the presence of the dead element and adjust the beamforming parameters to compensate for the loss. One such technique is disclosed in U.S. Pat. No. 5,676,149 to Yao. The second is to detect the failure during or after the manufacturing process and connect the missing element with a functional one, thereby reducing or eliminating the effect of the failure.

SUMMARY OF THE INVENTION

The present invention is a method and an apparatus for compensating for fully or partially inoperative elements in an ultrasonic transducer array. The inoperative elements are compensated for by "bridging" or "shorting" them to fully operative adjacent elements. This compensation technique can be applied to one-dimensional or multi-dimensional transducer arrays. While this technique is not the optimal solution from the imaging standpoint, it enables the loosening of manufacturing tolerances, thereby providing more cost-efficient manufacturing.

In accordance with the preferred embodiment of the invention, an ultrasonic probe is provided with multiplexer switches for connecting adjacent transducer elements as required, on-board flash (nonvolatile) memory for storing MUX State control data for controlling the state of the multiplexer switches and a dedicated microcontroller which loads and retrieves the MUX State control data into and from the flash memory. In response to detection of dead or weak elements by the master controller, new MUX State control data is sent from a flash memory programmer in the system to the microcontroller on-board the probe. The flash memory programmer in turn receives the new MUX State control data from the master controller after the latter has performed a diagnostic routine to identify any dead or weak elements in the transducer array. The flash memory programmer reconfigures the new MUX State control data into the format required for loading into the flash memory on-board the probe.

In accordance with the preferred embodiment, a bridge between a fully or partially inoperative element and an adjacent fully operative element is achieved by electrically connecting the elements via a switch of the multiplexer. Transducer elements which are not fully operative can be detected by analyzing the signals produced by each transducer element. If an element produces a weak or no signal, it is assumed that the transducer element is not fully operative. The on-board microcontroller uses the new MUX State control data to set the multiplexer switches so as to compensate for any detected dead or weak elements in the transducer array. This arrangement allows for automatic compensation of elements which are made defectively or become defective after manufacture.

Alternatively, a bridge between a fully or partially inoperative element and an adjacent fully operative element can be achieved by physically shorting the elements somewhere in the signal chain. A conventional ultrasonic probe comprises a transducer package which is supported within a probe housing. The transducer package comprises an array of transducer elements made of piezoelectric ceramic material. Typically, each transducer element has a metallic coating on opposing front and back faces. The metallic coating on the front face serves as the ground electrode. The ground electrodes of the transducer elements are all connected to a common ground. The metallic coating on the back face serves as the signal electrode. The signal electrodes of the transducer elements are connected to respective conductive traces formed on a flexible printed circuit board. Thus, adjacent elements can be shorted by connecting either the signal electrodes or the conductive traces associated with the adjacent elements. This repair operation can be performed following diagnostic testing performed during the production process or in the field.

The present invention is of use in two scenarios. The first is on the manufacturing line, where the ability to improve the performance of the probe in the presence of dead or weak elements may lead to an increased yield and lower cost during the production cycle. A secondary benefit may be achieved through the ability to calibrate the probes after field use, either in the field, at the factory, or at a remote service location.

DETAILED DESCRIPTION OF THE PREFERRED EMBODIMENTS

Figure 1:
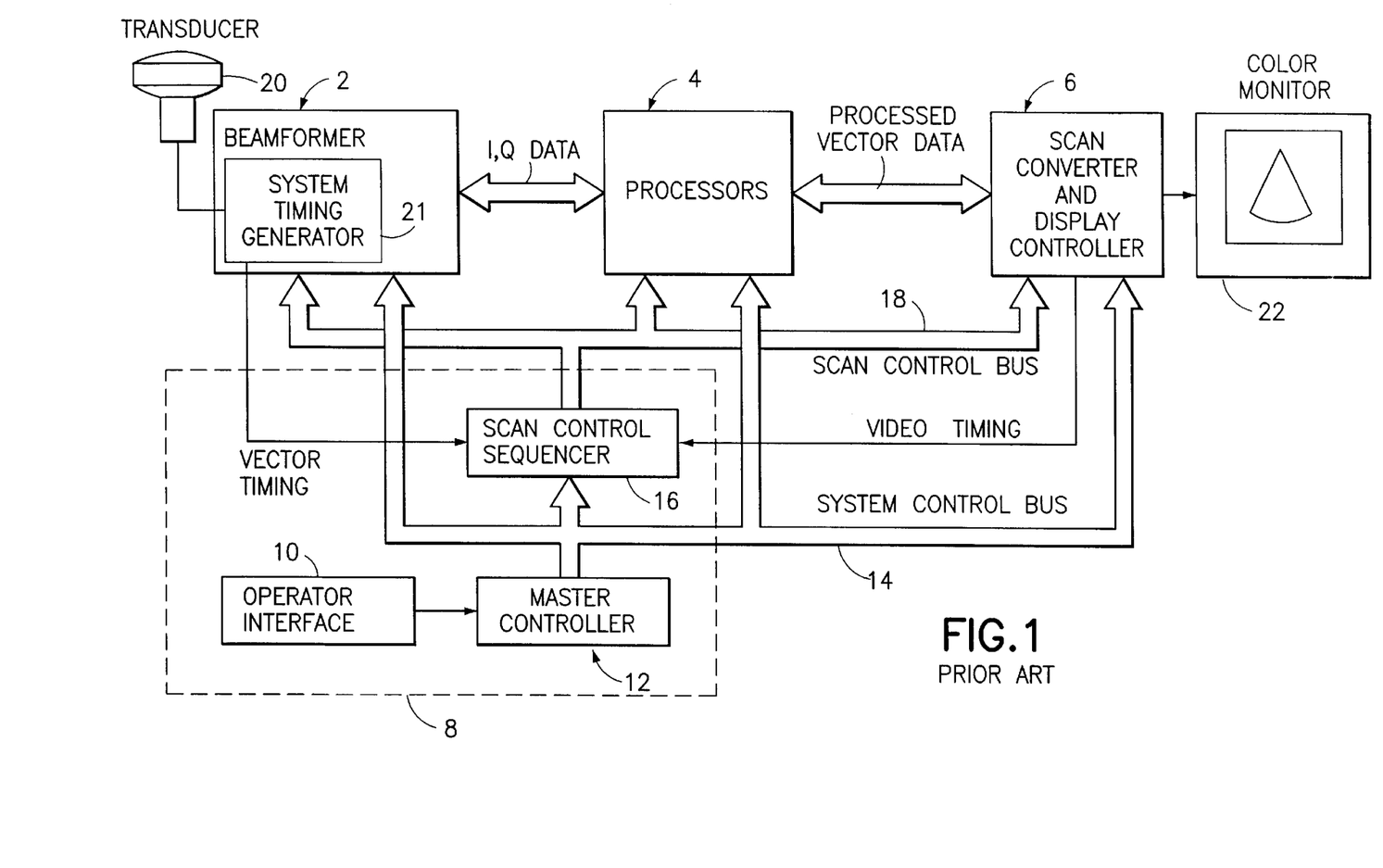
FIG. 1 is a block diagram of an ultrasound imaging system in which the present invention is incorporated.

FIG. 1 depicts an ultrasound imaging system consisting of four main subsystems: a beamformer 2, processors 4 (including a separate processor for each different mode), a scan converter/display controller 6 and a kernel 8. System control is centered in the kernel, which accepts operator inputs through an operator interface 10 and in turn controls the various subsystems. The master controller 12 performs system level control functions. It accepts inputs from the operator via the operator interface 10 as well as system status changes (e.g., mode changes) and makes appropriate system changes either directly or via the scan controller. The system control bus 14 provides the interface from the master controller to the subsystems. The scan control sequencer 16 provides real-time (acoustic vector rate) control inputs to the beamformer 2, system timing generator 24, processors 4 and scan converter 6. The scan control sequencer 16 is programmed by the host with the vector sequences and synchronization options for acoustic frame acquisitions. The scan converter broadcasts the vector parameters defined by the host to the subsystems via scan control bus 18.

The main data path begins with the analog RF inputs to the beamformer 2 from the transducer 20. The beamformer 2 outputs data to a processor 4, where it is processed according to the acquisition mode. The processed data is output as processed vector (beam) data to the scan converter/display controller 6. The scan converter accepts the processed vector data and outputs the video display signals for the image to color monitor 22.

Figure 2:
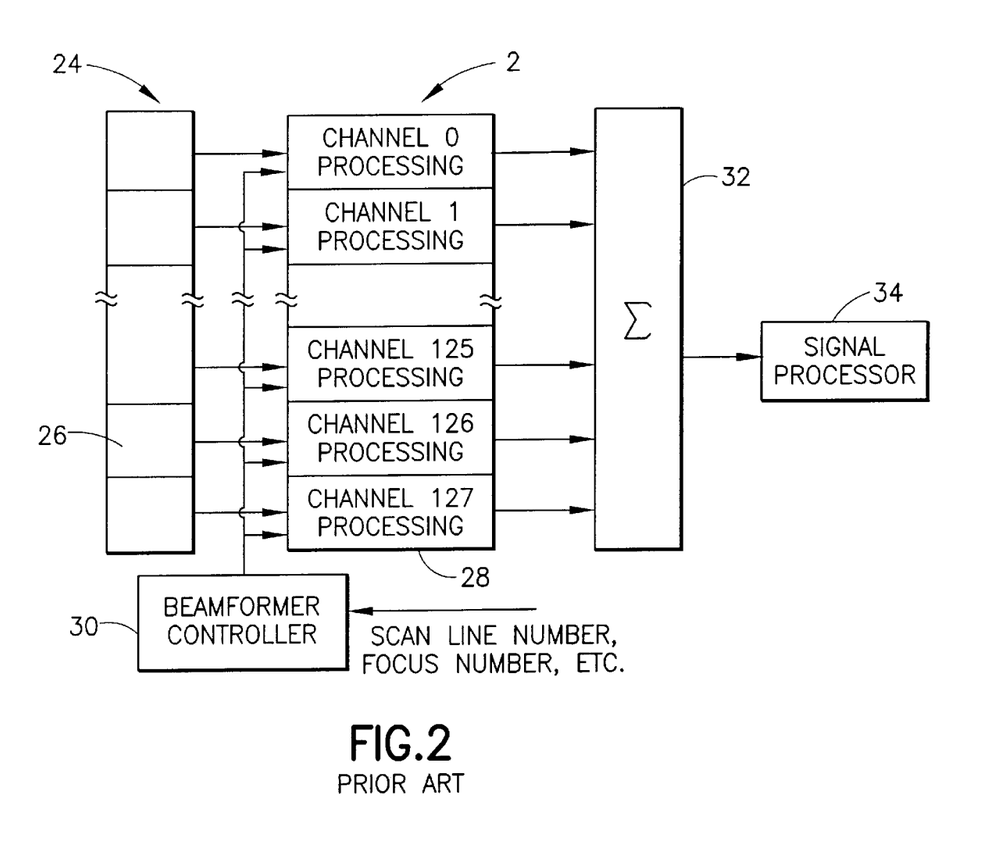
FIG. 2 is a block diagram of a typical 128-channel beamformer in a conventional ultrasound imaging system.

Referring to FIG. 2, a conventional ultrasound imaging system includes a transducer array 24 comprised of a plurality of separately driven transducer elements 26, each of which produces a burst of ultrasonic energy when energized by a pulsed waveform produced by a transmitter (not shown). The ultrasonic energy reflected back to transducer array 24 from the object under study is converted to an electrical signal by each receiving transducer element 26 and applied separately to beamformer 2.

The echo signals produced by each burst of ultrasonic energy reflect from objects located at successive ranges along the ultrasonic beam. The echo signals are sensed separately by each transducer element 26 and the magnitude of the echo signal at a particular point in time represents the amount of reflection occurring at a specific range. Due to the differences in the propagation paths between an ultrasound-echo-producing sample volume and each transducer element 26, however, these echo signals will not be detected simultaneously and their amplitudes will not be equal. Beamformer 2 amplifies the separate echo signals, imparts the proper time delay to each, and sums them to provide a single echo signal which accurately indicates the total ultrasonic energy reflected from the sample volume. Each beamformer channel 28 receives the analog echo signal from a respective transducer element 26.

To simultaneously sum the electrical signals produced by the echoes impinging on each transducer element 26, time delays are introduced into each separate beamformer channel 28 by a beamformer controller 30. The beam time delays for reception are the same delays as the transmission delays. However, the time delay of each beamformer channel is continuously changing during reception of the echo to provide dynamic focusing of the received beam at the range from which the echo signal emanates. The beamformer channels also have circuitry (not shown) for apodizing and filtering the received pulses.

The signals entering the summer 32 are delayed so that when they are summed with delayed signals from each of the other beamformer channels 28, the summed signals indicate the magnitude and phase of the echo signal reflected from a sample volume located along the steered beam. A signal processor or detector 34 converts the received signal to display data. In the B-mode (gray-scale), this would be the envelope of the signal with some additional processing such as edge enhancement and logarithmic compression. The scan converter 6 receives the display data from detector 34 and converts the data into the desired image for display. This scan-converted acoustic data is then output for display on display monitor 22, which images the time-varying amplitude of the envelope of the signal as a gray scale.

Figure 3:
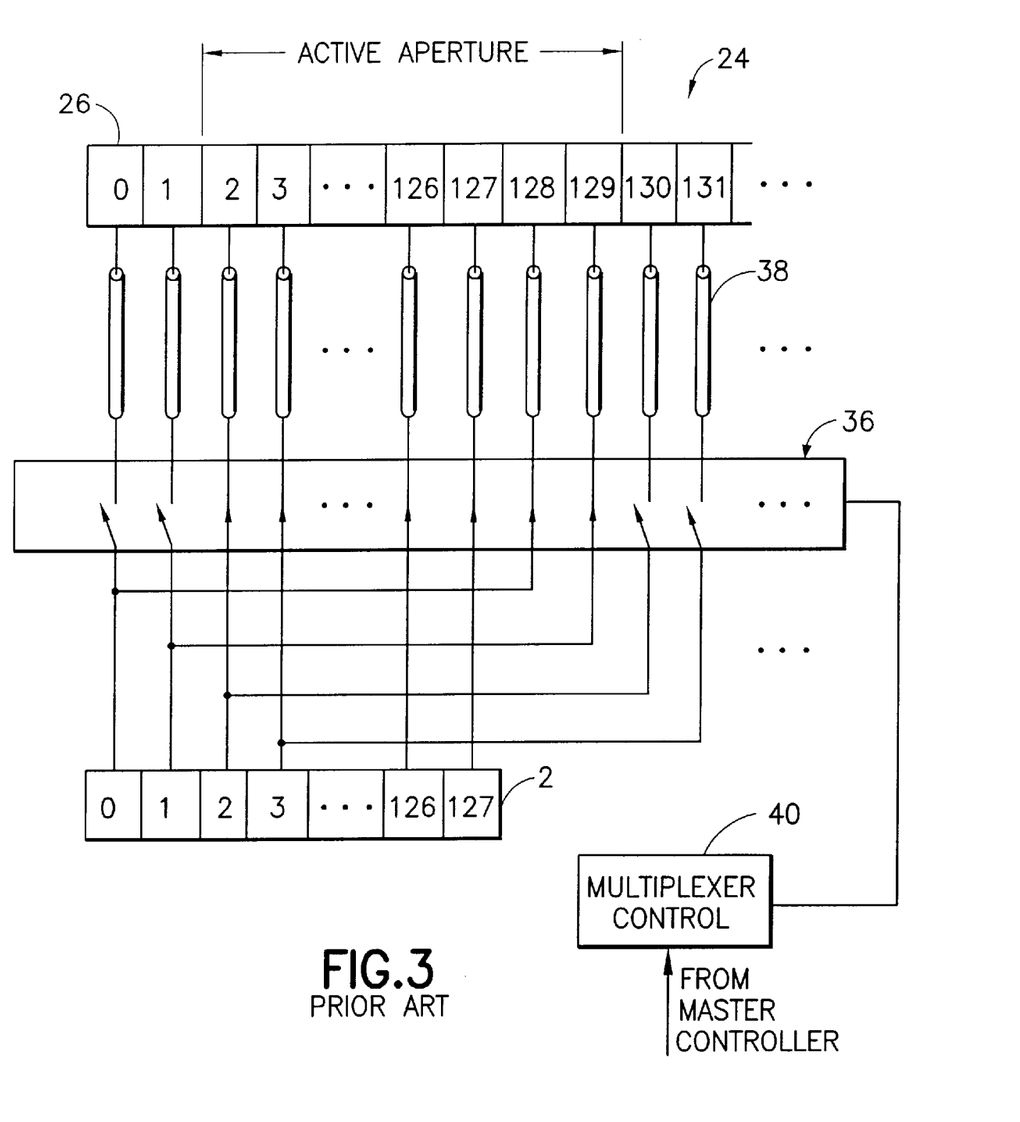
FIG. 3 is a schematic of a conventional arrangement in which a multiplexer is connected between a set of beamformer channels and a 1D transducer array having a number of elements greater than the number of beamformer channels.

A typical one-dimensional linear or convex transducer array and multiplexer is shown schematically in FIG. 3. The beamformer 2 has 128 beamformer channels, but the transducer array 24 has significantly more elements (typically 192 to 256). The multiplexer 36 allows any set of up to 128 contiguous transducer elements 26 to be simultaneously connected to the beamformer channels 28 via coaxial cable bundles 38. By closing switches connected to elements 0 through 127, the beamformer 2 is connected to the left end of the transducer array and focused beams of ultrasound may be transmitted and received to acquire data for the corresponding edge of the image. As the point of origin of successive ultrasound beams steps along the transducer array 24 to the right, it becomes advantageous to shift the active aperture so that the origin of the ultrasound beam is centered within it. To shift the aperture from the extreme left end of the array by one element toward the right, the multiplexer switch connected to element 0 is opened and the switch connected to element 128 is closed. This shifts beamformer channel 0 from the left end to the right end of the active aperture, while leaving all other channels and elements connected as before. The time delays and other beamforming parameters are changed by the software to correspond to the new multiplexer state and one or more additional image vectors are acquired. Then the aperture is stepped further to the right, by opening the switch connected to element 1 and closing the switch connected to element 129, leaving the multiplexer 36 in the state shown in FIG. 3. In this manner the active aperture can be stepped sequentially from one end of the transducer array 24 to the other. Alternatively, the same multiplexer hardware may be used to scan the active aperture more rapidly across the array by switching several transducer elements per step. In some imaging modes, successive apertures may be selected non-sequentially, jumping back and forth between the left and right ends of the transducer array. The state of multiplexer 36 is controlled by a multiplexer control board 40. The multiplexer control board 40 receives a MUX State command from the master controller 12 (see FIG. 1) and uses data stored in on-board memory (ROM or EEPROM) to set every switch in multiplexer 36 to the open or closed position required for the commanded multiplexer state.

During the process of manufacturing an ultrasonic transducer array, it is possible to detect weak or dead elements during the testing cycle. At this time, using known soldering or electrical connection techniques, it is possible to directly electrically connect weak or dead elements to adjacent fully operative elements in order to compensate for the defect. As a result of this arrangement, each of the beamformer receive channels corresponding to the electrically connected transducer elements will receive a signal which is the sum of the signals produced by the electrically connected transducer elements. The electrical connection might take the form of a bridge wire on a flex circuit or a solder or conductive epoxy bridge on the ceramic. Alternatively, the electrical connection could be established in the system connector. This methodology can be applied to any one-dimensional or multi-dimensional (including 1.25D, 1.5D, 1.75D and 2D) arrays.

Figure 4:
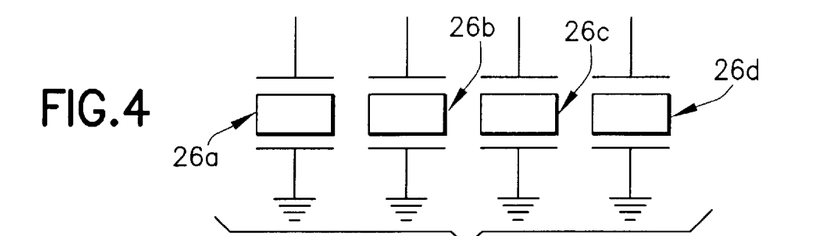
FIG. 4 is a schematic showing a plurality of adjacent elements of a 1D ultrasonic transducer array.

FIG. 4 shows a plurality of adjacent elements 26a–26d of a 1D transducer array 24A. For the purpose of discussion, it will be assumed that element 26b is fully or partially inoperative, while elements 26a, 26c and 26d are fully operative.

Figure 5:
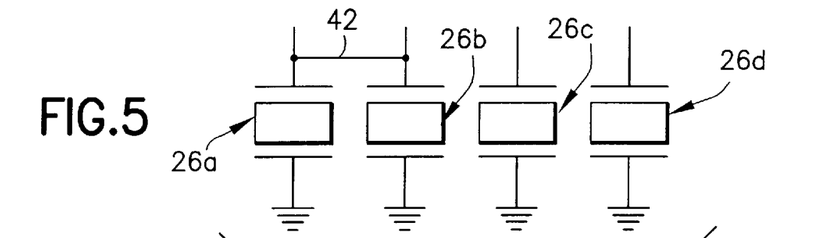
FIGS. 5 and 6 are schematics showing a plurality of adjacent elements of a 1D transducer array in which an inoperative element is directly electrically connected to an adjacent operative element (FIG. 5) or to two adjacent operative elements (FIG. 6) in accordance with one preferred embodiment of the invention.

In accordance with a preferred embodiment of the invention shown in FIG. 5, the defective element 26b can be compensated for by establishing a direct electrically conductive connection 42 between fully operative element 26a and defective element 26b. Alternatively, defective element 26b could be directly electrically connected to fully operative element 26c.

Figure 6:
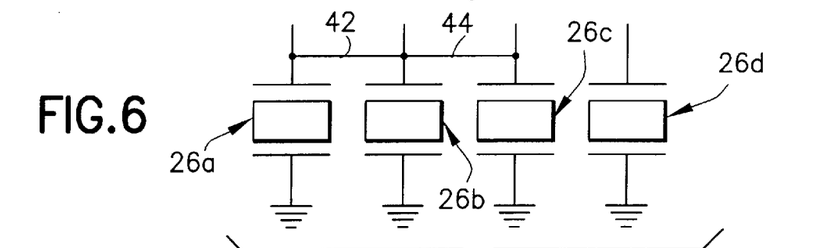

In accordance with a variation of the above-described preferred embodiment shown in FIG. 6, the defective element 26b can be compensated for by establishing a direct electrically conductive connection 42 between fully operative element 26a and defective element 26b as well as a direct electrically conductive connection 44 between fully operative element 26c and defective element 26b.

Figure 7:
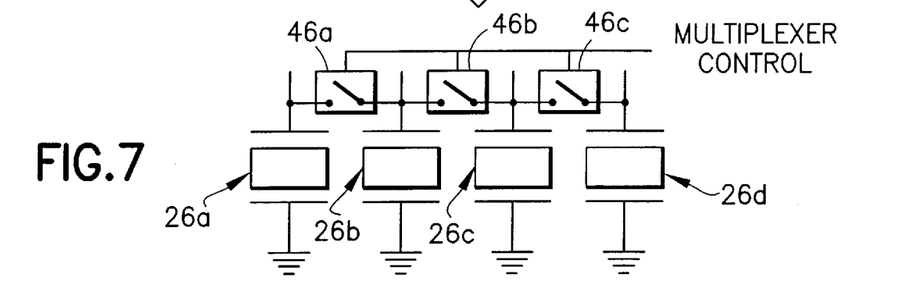
FIGS. 7 and 8 are schematics showing another preferred embodiment in which adjacent elements of a 1D transducer array are selectively electrically connectable by closure of a respective switch of a multiplexer. The inoperative element is shown electrically connected (FIG. 8) and not electrically connected (FIG. 7) to an adjacent operative element.

An alternative technique for implementing the invention is to design a multiplexing circuit for use alone or in combination with an existing multiplexer such that the bridging option can be controlled electronically based on the results of diagnostic testing. In accordance with a further preferred embodiment, the master controller monitors the operative status of each transducer element and automatically compensates for a detected defective element by causing one or more associated switches of the multiplexer to be closed. For example, the compensation function can be implemented by providing a multiplexer having a bank of selectively controllable (i.e., electronically controlled) switches, each multiplexer switch being arranged to bridge a respective pair of adjacent transducer elements when the switch is closed. FIG. 7 shows an exemplary arrangement wherein a first multiplexer switch 46a selectively electrically connects elements 26a and 26b; a second multiplexer switch 46b selectively electrically connects elements 26b and 26c; and a third multiplexer switch 46c selectively electrically connects elements 26c and 26d. It should be appreciated that this arrangement can be extended in the azimuth direction indefinitely, i.e., for any number of transducer elements.

Figure 8:
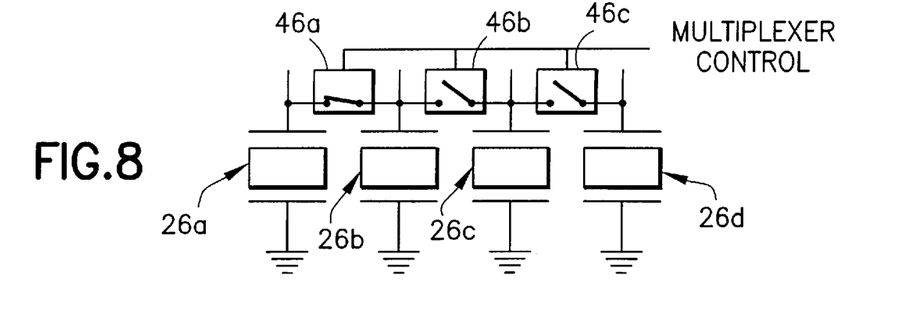

FIG. 8 depicts the situation wherein a defective transducer element 26b has been compensated for by closing multiplexer switch 46a, thereby electrically connecting element 26b to fully operative transducer element 26a. (Multiplexer switch 46a could also be closed in response to detection that element 26a, instead of element 26b, was defective.) As an alternative to closing multiplexer switch 46a to compensate for element 26b being defective, multiplexer switch 46b could be closed, thereby electrically connecting element 26b to fully operative transducer element 26c instead of element 26a.

The same techniques used for compensating for the loss of the elements in the azimuth direction (i.e., the one-dimensional case) are applicable in the two-dimensional case. Now a defective element can be directly connected to one of four contiguous neighbors, effectively reducing the amplitude differential between the elements. However, in order to maintain the peak performance in the azimuthal plane, the preferred embodiment is to connect elements in the elevation direction only, not in the azimuth direction. This results in an effective element which has the same azimuthal dimension as the other elements, limiting the difference to the elevation plane.

Figure 9:
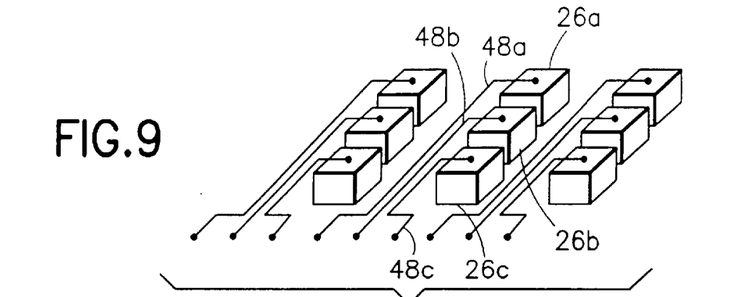
FIG. 9 is a schematic showing a plurality of adjacent elements of a 2D ultrasonic transducer array.

FIG. 9 shows a 3×3 subarray of adjacent elements of a 2D transducer array 24B, with elements of the second column being designated 26a, 26b and 26c. Again it will be assumed that element 26b is fully or partially inoperative, while elements 26a and 26c are fully operative. Each of elements 26a–26c is electrically connected to the system connector (not shown) via respective conductors 48a–48c.

Figure 10:
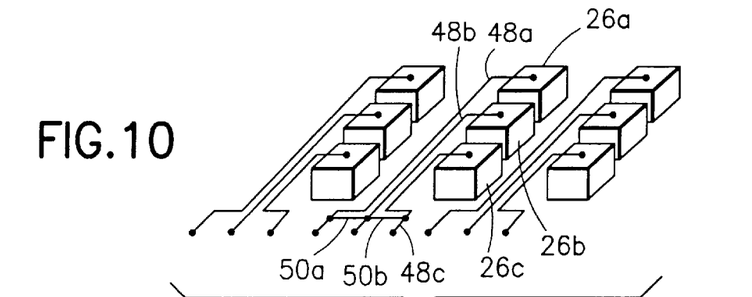
FIG. 10 is a schematic showing a plurality of adjacent elements of a 2D transducer array in which an inoperative element is directly electrically connected to two adjacent operative elements in the elevation direction in accordance with a further preferred embodiment of the invention.

In accordance with another preferred embodiment of the invention shown in FIG. 10, the defective element 26b can be compensated for by establishing a direct electrically conductive connection 50a between conductors 48a and 48b or a direct electrically conductive connection 50b between conductors 48b and 48c or both. The connection 50a shorts defective element 26b to fully operative element 26a, while the connection 50b shorts defective element 26b to fully operative element 26c. When conductors 48a and 48b are electrically connected by connection 50a, the beamformer channels corresponding to elements 26a and 26b each receive the sum of the receive signals from those two elements. During transmission, elements 26a and 26b will receive the same transmit pulse waveform. Similarly, when conductors 48a, 48b and 48c are electrically connected by connections 50a and 50b, the beamformer channels corresponding to elements 26a, 26b and 26c each receive the sum of the receive signals from those three elements. Again during transmission, elements 26a–26c will receive the same transmit pulse waveform.

Although FIG. 10 depicts the connection of a defective transducer element 26b to adjacent transducer elements in the elevation direction, it will be appreciated that, in the alternative, transducer element 26b could be connected to adjacent transducer elements in the azimuth direction.

In accordance with an alternative preferred embodiment, the electrical conductors corresponding to adjacent transducer elements in the elevation direction can be selectively connected using multiplexer switches. For example, multiplexer switches could be incorporated in place of connections 50a and 50b in FIG. 10 and also could be used to selectively connect the conductors associated with adjacent transducer elements in other columns.

Figure 11:
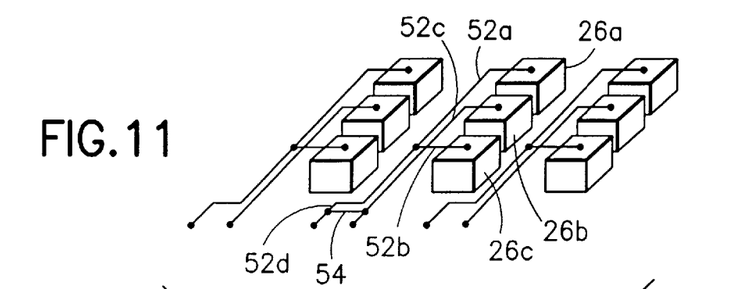
FIG. 11 is a schematic showing a plurality of adjacent elements of a 1.5D transducer array in which an inoperative element in a center row is directly connected to two adjacent operative elements in the elevation direction in accordance with another preferred embodiment of the invention.

FIG. 11 shows a 3×3 subarray of adjacent elements of a 1.5D transducer array 24C, with elements of the second column again designated 26a, 26b and 26c, and element 26b being in the center row of the 1.5D array. In a 1.5D array, the transducer elements in each row other than the center row are electrically linked to the corresponding transducer elements in the symmetrically arranged row on the other side of the center row, e.g., element 26a is electrically linked to element 26c via electrical conductors 52a and 52c in FIG. 11. The junction connecting conductors 52a and 52c is in turn connected to the system connector via an electrical conductor 52d, while element 26b of the center row is connected to the system connector via an electrical conductor 52e. Again it will be assumed that element 26b is fully or partially inoperative, while elements 26a and 26c are fully operative.

In accordance with the preferred embodiment of the invention shown in FIG. 11, the defective element 26b can be compensated for by establishing a direct electrically conductive connection 54 between conductors 52c and 52d. The connection 54 shorts defective element 26b to fully operative elements 26a and 26c. When conductors 52c and 52d are electrically connected by connection 54, the beamformer channels corresponding to elements 26a, 26b and 26c each receive the sum of the receive signals from those three elements. During transmission, elements 26a–26c will receive the same transmit pulse waveform.

Figure 12:
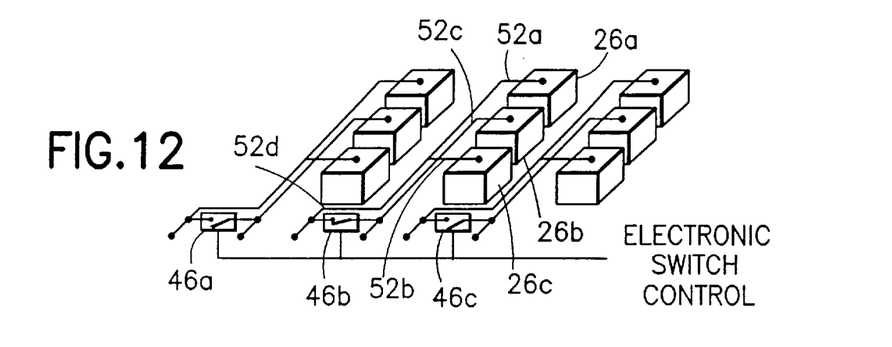
FIG. 12 is a schematic showing a plurality of adjacent elements of a 1.5D transducer array in which an inoperative element in a center row is selectively electrically connectable to two adjacent operative elements in the elevation direction by closure of a respective switch of a multiplexer in accordance with a further preferred embodiment of the invention.

In accordance with an alternative preferred embodiment for use with 1.5D arrays, the electrical conductor associated with the element in the center row and the i-th column can be connected to the electrical conductor linking the elements in the i-th column adjacent to the center row element in the i-th column by means of a multiplexer switch. For example, FIG. 12 shows three multiplexer switches 46a–46c associated with respective columns of a 1.5D array. Switch 46b is closed to compensate for the defective element 26a, i.e., by electrically connecting element 26a to linked fully operative elements 26a and 26c. Electrical control means must be provided to the switches in order to configure the probe either on the production line or in the field if elements fail during normal use of the product.

Figure 13:
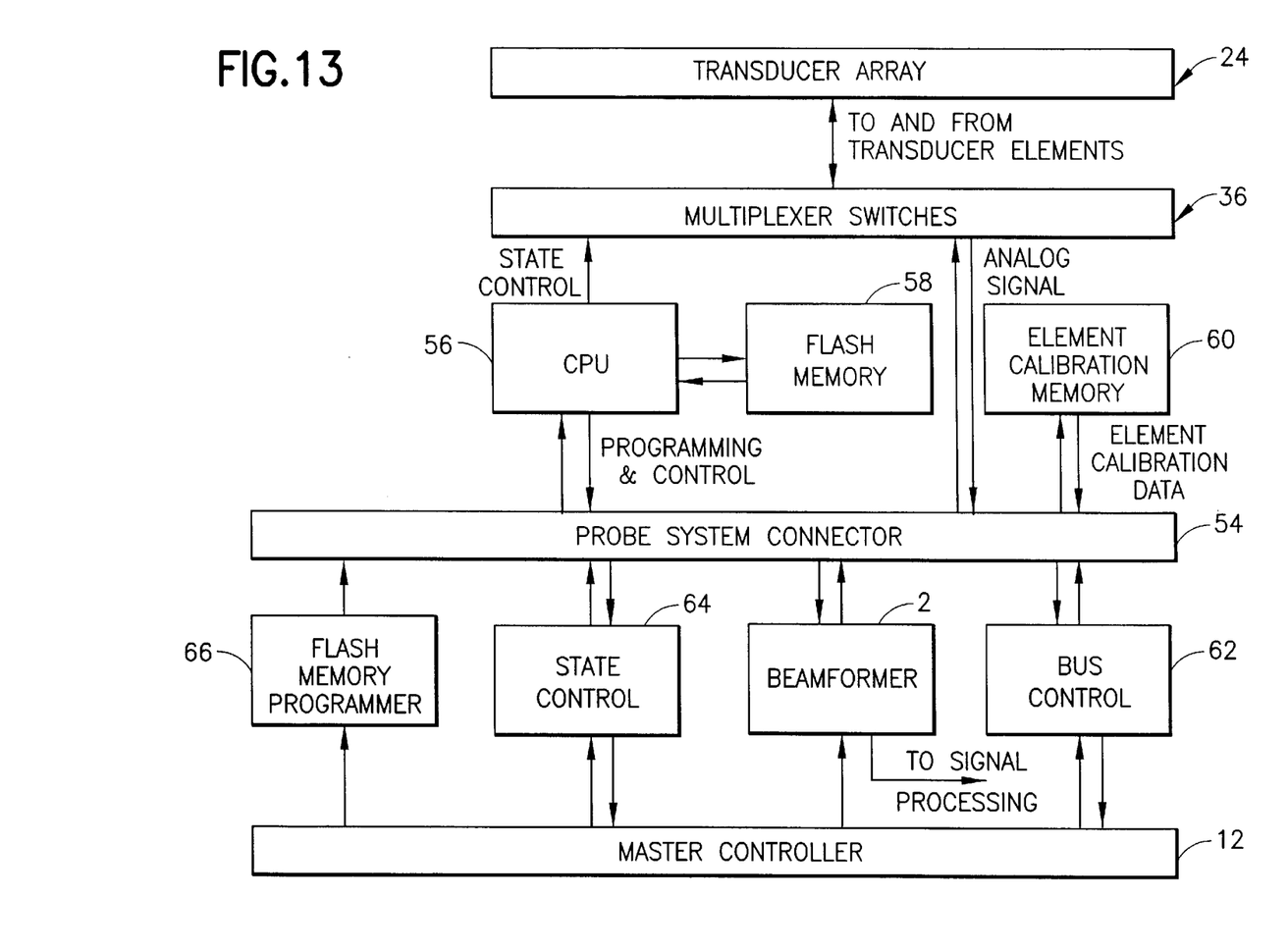
FIG. 13 is a block diagram showing a programmable probe connected to an ultrasound imaging system in accordance with a preferred embodiment of the invention.

A preferred embodiment of the invention can be configured as shown in FIG. 13. An ultrasonic probe comprising an array 24 of ultrasonic transducer elements is connected to an ultrasound imaging system by a probe/system connector 54. The probe/system connector comprises a multiplicity of electrically conductive connections connected at one end to respective transmit/receive (T/R) switches (not shown) of a beamformer 2 and at the other end to various subsets of multiplexer switches 36. In addition to switches for connecting transducer elements to beamformer receive channels, the multiplexer 36 includes switches for connecting adjacent transducer elements to each other.

The beamformer 2 is operated under control of the master controller 12, which provides apodization weighting factors and time delays to the beamformer in both the transmit and receive modes. Under the direction of the master controller 12, the transmit beamformer drives transducer array 24 such that the ultrasonic energy is transmitted as a directed focused beam. To accomplish this, respective time delays are imparted to a multiplicity of pulsers (not shown) incorporated in beamformer 4. The master controller determines the conditions under which the acoustic pulses will be transmitted. With this information, the transmit beamformer will determine the timing and the amplitudes of each of the transmit pulses to be generated by the pulsers. The pulsers in turn send the transmit pulses to each of the elements of the transducer array 24 via the T/R switches, the probe/system connector 54 and the multiplexer switches 36. By appropriately adjusting the transmit focus time delays and the apodization weightings in a conventional manner, an ultrasonic beam can be directed and focused to form a transmit beam.

The echo signals produced by each burst of ultrasonic energy reflect from objects located at successive ranges along each transmit beam. The echo signals are sensed separately by each transducer element. Due to the differences in the propagation paths between a reflecting point and each transducer element, the echo signals will not be detected simultaneously and their amplitudes will not be equal. The receive beamformer amplifies the separate echo signals in each receive channel. Under the direction of the master controller 12, the receive beamformer tracks the direction of the transmitted beam, sampling the echo signals at a succession of ranges along each beam. The receive beamformer imparts the proper time delays and receive apodization weightings to each amplified echo signal and sums them to provide an echo signal which accurately indicates the total ultrasonic energy reflected from a point located at a particular range along one ultrasonic beam.

As seen in FIG. 13, the probe further comprises a flash (nonvolatile) memory 58 for storing MUX State control data for controlling the state of the multiplexer switches 36 and a CPU 56 which serves as a dedicated microcontroller for loading and retrieving MUX State control data into and from the flash memory. The CPU 56 interfaces with a flash memory programmer 66 via the probe/system connector 54. In accordance with the present invention, new MUX State control data containing switch settings for connecting a defective transducer element to an adjacent fully functional element is output to CPU 56 by flash memory programmer 66. The flash memory programmer in turn receives new MUX State control data from the master controller 12, albeit in a format not suitable for loading into the flash memory 58. The flash memory programmer 66 reconfigures the new MUX State control data into the format required by flash memory 58. The master controller 12 computes new MUX State control data after performing a diagnostic routine which detects dead or weak elements in the transducer array 24.

In accordance with a preferred embodiment of the invention, a MUX State control signal is output by the master controller 12 to a state control device 64. The MUX State control signal configures the probe with a desired aperture. In response to the MUX State control signal, the state control device 64 sets a register on the probe/system connector 54. The CPU 56 reads that register to determine the desired MUX State and then retrieves the MUX State control data corresponding to that state from the flash memory 58. The multiplexer switches 36 are then set by the corresponding MUX State control signals output from CPU 60. Alternatively, the CPU 56 can provide address signals and a read signal which allow the MUX State control signals to be sent directly from the flash memory 58 to the multiplexer 36.

The probe system also includes an element calibration memory 60, which stores the individual transducer element performance data, i.e., amplitude and phase information. This amplitude and phase information characterizes the particular probe being used. When the probe is connected to an ultrasound imaging system (as shown in FIG. 13), the serial bus control device 62 reads the element amplitude and phase information from memory 60 and outputs it to the master controller, which uses that information to calibrate the beamformer 2 for amplitude and phase differences between elements.

The flash memory 58 and element calibration memory 60 are both initially loaded on the probe manufacturing line. Reprogramming of one or both memories can be done on the manufacturing line or in the field. In accordance with a preferred embodiment, the flash memory 62 can be reprogrammed to compensate for dead or weak elements in the transducer array 24. If dead or weak elements are detected during quality control inspections on the manufacturing line, the flash memory is reprogrammed at a programming station. After this process, calibration of the transducer elements is completed and the element calibration data is loaded into the element calibration memory 64. Alternatively, if dead or weak elements are detected in the field using a diagnostic program run by the master controller, the flash memory is reprogrammed by the master controller via flash memory programmer. Then the element calibration memory 60 is reprogrammed via the bus control device 62. In either case, the reprogramming of the flash memory 58 enables the CPU 60 to close multiplexer switches 36 of the type shown in FIGS. 7, 8 and 12 in order to electrically connect a dead or weak element to an adjacent fully operative element.

As the element count in two-dimensional probes increases dramatically, the difficulties associated with delivering a "no dead element" probe from manufacturing are daunting. However, with the increased element count comes some redundancy and, in some cases, some latitude with respect to dead elements. In simple terms, increasing the element count by a factor of 4 or 5 means that a single dead element constitutes a smaller percentage of the total number of elements. While this view holds in the case of full aperture imaging, it does not support the case where the aperture used for imaging is the same size as that of the one-dimensional case. This occurs at close range where the aperture size is reduced in both elevation and azimuth. Thus there is a need for a technique by which dead or weak transducer elements can be compensated for. That need is satisfied by the present invention.

The foregoing preferred embodiments have been disclosed for the purpose of illustration. Variations and modifications will be readily apparent to persons skilled in the art. For example, it will be apparent to a person skilled in the art that a defective transducer element could be connected to a diagonally located element, instead of a contiguous element in the same row or same column of the array. All such variations and modifications are intended to be encompassed by the claims set forth hereinafter.

What is claimed is:

1. An ultrasound imaging system comprising:
   a transducer array comprising first and second transducer elements, said second transducer element being adjacent to said first transducer element;
   an electronically controlled switch having a first junction electrically connected to said first transducer element and a second junction electrically connected to said second transducer element, said electronically controlled switch having a first switching state for electrically connecting said first and second transducer elements to each other and to a terminal and having a second switching state for not electrically connecting said first and second transducer elements to each other;

a memory storing a switching state control datum indicating a selected one of said first and second switching states of said electronically controlled switch;

a controller programmed and connected to control the switching state of said electronically controlled switch as a function of said switching state control datum;

a computer programmed to perform the following steps:
(a) diagnosing a defective state of said first transducer element;
(b) forming a switching state control datum indicating selection of said first switching state in response to said step of diagnosing said defective state of said first transducer element; and
(c) sending said switching state control datum indicating selection of said first switching state to said controller, wherein said controller is further programmed to load said switching state control datum indicating selection of said first switching state into said memory following said sending steps;

a pulser for sending a transmit pulse to said electronically controlled switch in a transmit mode;

a receive channel for receiving an echo signal from said electronically controlled switch in a receive mode;

a signal processing subsystem for forming an image signal which is a function of at least said echo signal; and a display device for displaying an image having a portion representing said image signal.

2. The ultrasound imaging system as recited in claim 1, further comprising a probe and a probe/system connector for operatively coupling said probe to said computer, wherein said transducer array, said memory and said controller are incorporated in said probe.

3. An ultrasound imaging system comprising:

a transducer array comprising first and second transducer elements, said second transducer element being adjacent to said first transducer element;

an electronically controlled switch having a first junction electrically connected to said first transducer element and a second junction electrically connected to said second transducer element, said electronically controlled switch having a first switching state for electrically connecting said first and second transducer elements to each other and to a terminal and having a second switching state for not electrically connecting said first and second transducer elements to each other;

diagnostic means for monitoring said first and second transducer elements to detect a defective state;

control means for changing the state of said first electronically controlled switch from said second switching state to said first switching state in response to said diagnostic means detecting a defective state in one of said first and second transducer elements;

a pulser for sending a transmit pulse to said electronically controlled switch in a transmit mode;

a receive channel for receiving an echo signal from said electronically controlled switch in a receive mode;

a signal processing subsystem for forming an image signal which is a function of at least said echo signal; and a display device for displaying an image having a portion representing said image signal.

4. A beamforming system comprising:

a beamformer comprising first and second beamformer channels and a computer for controlling beamforming in said first and second beamforming channels in accordance with a beamforming program;

a transducer array comprising first and second transducer elements, said second transducer element being adjacent to said first transducer element;

a first electronically controlled switch arranged to electrically connect said first transducer element to said first beamformer channel in a closed state;

a second electronically controlled switch arranged to electrically connect said second transducer element to said second beamformer channel in a closed state;

a third electronically controlled switch arranged to electrically connect said first transducer element to said second transducer element in a closed state;

a controller for opening and closing said first, second and third electronically controlled switches in accordance with switching instructions from said computer;

first and second pulsers for sending respective transmit pulses on said first and second beamformer channels in a transmit mode; and a beamsummer for receiving respective echo signals from said first and second beamformer channels in a receive mode, wherein said computer is programmed to perform the following steps:
(a) monitoring said first and second transducer elements to detect a defective state; and
(b) outputting a set of switching instructions to said controller for closing said third electronically controlled switch in either of said transmit and receive modes only if one of said first and second transducer elements is in a defective state.

5. The beamforming system as recited in claim 4, wherein each of said transducer elements comprises piezoelectric material.

6. A method for compensating for a defective transducer element in an array of transducer elements, comprising the steps of:

detecting the state of each of said transducer elements;

identifying a transducer element which is defective; and electrically shorting said defective transducer element to a fully operative transducer element.

7. The method as recited in claim 6, wherein said electrically shorting step is carried out by closing an electronically controlled switch.

8. The method as recited in claim 6, wherein each of said transducer elements comprises piezoelectric material.

9. A system for configuring an array of transducer elements in which each transducer element has at least one other transducer element adjacent thereto, comprising:

a multiplicity of electronically controlled switches arranged to selectively electrically connect adjacent transducer elements to each other;

means for detecting the presence of defective transducer elements; and means for closing one of said multiplicity of electronically controlled switches in response to detection of a defective transducer element, said closed electronically controlled switch electrically connecting said defective transducer element and a non-defective transducer element adjacent to said defective transducer element.

10. The system as recited in claim 9, wherein each of said transducer elements comprises piezoelectric material.

11. A system comprising:

a transducer array comprising a multiplicity of transducer elements;

means for detecting the state of each of said transducer elements;

means for identifying a transducer element which is defective; and means for electrically shorting said defective transducer element to a fully operative transducer element.

12. The system as recited in claim 11, wherein each of said transducer elements comprises piezoelectric material.

13. The system as recited in claim 11, wherein said means for electrically shorting comprise an electronically controlled switch.

14. An apparatus comprising an ultrasonic probe, an ultrasound imaging system and a probe/system connector for connecting said probe to said system, wherein said probe comprises an array of transducer elements in which each transducer element has at least one other transducer element adjacent thereto, a multiplicity of electronically controlled switches respectively arranged to connect adjacent transducer elements to each other when said switches are closed and programmable means controlling the states of said multiplicity of electronically controlled switches as a function of switching state control data; and wherein said system comprises diagnostic means for monitoring said transducer elements to detect the presence of defective transducer elements, and means for programming said programmable means with predetermined state control data in response to detection of a defective transducer element, said predetermined state control data programming said programmable means to close a selected one of said multiplicity of electronically controlled switches which electrically connects said defective transducer element and a non-defective transducer element adjacent to said defective transducer element.

15. A probe comprising:

an array of transducer elements in which each transducer element has at least one other transducer element adjacent thereto;

a multiplicity of electronically controlled switches respectively arranged to connect adjacent transducer elements to each other when said switches are closed; and programmable means programmed to control the states of said multiplicity of electronically controlled switches in accordance with switching state control data, wherein at least one of said transducer elements is defective, and said switching state control data programs said programmable means to close a selected one of said multiplicity of electronically controlled switches which electrically connects said defective transducer element and a non-defective transducer element adjacent to said defective transducer element.

16. The probe as recited in claim 15, wherein each of said transducer elements comprises piezoelectric material.

17. A probe comprising:

an array of transducer elements in which each transducer element has at least one other transducer element adjacent thereto, said array comprising a defective transducer element; and a permanent connection which electrically connects said defective transducer element and a non-defective transducer element adjacent to said defective transducer element.

18. The probe as recited in claim 17, wherein each of said transducer elements comprises piezoelectric material.

19. An imaging system comprising:

a transducer array comprising first and second transducer elements, said second transducer element being adjacent to said first transducer element;

a transmit beamformer for supplying transmit pulses to said first and second transducer elements in a transmit mode;

a receive beamformer for receiving echo signals from said first and second transducer elements in a receive mode;

an electronically controlled switch having a first junction electrically connected to said first transducer element and a second junction electrically connected to said second transducer element, said electronically controlled switch having a first switching state for electrically connecting said first and second transducer elements to each other and to a terminal and having a second switching state for not electrically connecting said first and second transducer elements to each other;

diagnostic means for monitoring said first and second transducer elements to detect a defective state;

control means for invoking said first switching state during beamforming if said diagnostic means has detected a defective state in one of said first and second transducer elements;

a signal processing subsystem for forming an image signal which is a function of at least an echo signal from a non-defective one of said first and second transducer elements; and a display device for displaying an image having a portion representing said image signal.

20. The imaging system as recited in claim 19, wherein each of said first and second transducer elements comprises piezoelectric material.

* * * * *